(12) United States Patent
Himmelsbach

(10) Patent No.: US 6,248,932 B1
(45) Date of Patent: Jun. 19, 2001

(54) SELF-ADHESIVE READY-MADE BANDAGE FOR RESTRICTING STRETCHING OR BENDING OF THE METACARPOPHALANGEAL JOINT AND OF THE WRIST

(75) Inventor: Peter Himmelsbach, Buxtehude (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/341,749

(22) PCT Filed: Jan. 17, 1998

(86) PCT No.: PCT/EP98/00251

§ 371 Date: Aug. 27, 1999

§ 102(e) Date: Aug. 27, 1999

(87) PCT Pub. No.: WO98/32405

PCT Pub. Date: Jul. 30, 1998

(30) Foreign Application Priority Data

Jan. 23, 1997 (DE) .............................................. 197 02 301
Jan. 23, 1997 (DE) .............................................. 197 02 302

(51) Int. Cl.[7] ...................................................... A61F 13/00
(52) U.S. Cl. ............................... 602/41; 602/42; 602/43; 602/44; 602/45; 602/46
(58) Field of Search .......................................... 602/41–47

(56) References Cited

U.S. PATENT DOCUMENTS

| 2,563,689 | 8/1951 | Muhlhauser | 128/156 |
| 2,875,758 | 3/1959 | Fuzak et al. | 128/157 |
| 3,880,159 | 4/1975 | Diamond | 128/157 |
| 3,971,374 | * 7/1976 | Wagner . | |
| 4,549,537 | 10/1985 | Ender | 128/87 |
| 5,267,952 | * 12/1993 | Gardner . | |

FOREIGN PATENT DOCUMENTS

| 734888 | 4/1943 | (DE) | 30/22 |
| 0039323 | 11/1981 | (EP) | A61F/5/04 |
| 752041 | 9/1933 | (FR) | 19/2 |

* cited by examiner

Primary Examiner—Michael A. Brown
Assistant Examiner—Lalita Hamilton
(74) Attorney, Agent, or Firm—Norris McLaughlin & Marcus

(57) ABSTRACT

Ready-made bandage with a self-adhesive coating on at least one side, for restricting stretching or bending of the metacarpophalangeal joint and/or of the wrist, wherein, at the head area (13) of an oblong strip (1), a short rein (41, 42) is arranged on at least one of the two longitudinal sides, encloses an angle of between 30° and 150° with the oblong strip (1) and is applied on the finger in question.

16 Claims, 2 Drawing Sheets

SELF-ADHESIVE READY-MADE BANDAGE FOR RESTRICTING STRETCHING OR BENDING OF THE METACARPOPHALANGEAL JOINT AND OF THE WRIST

The invention relates to a ready-made bandage with a selfadhesive coating on one side, for restricting stretching or bending of the metacarpophalangeal joint and of the wrist.

BACKGROUND OF THE INVENTION

The functional dressing technique called taping is a treatment method for prevention and therapy of injuries, diseases and lesions of the locomotor apparatus. The aim of taping is to purposefully simulate the capsular ligament structures and in so doing to achieve selective support and stabilizing.

The actual tape dressing is applied in strips made up of preferably non-elastic self-adhesive tapes, so-called reins, or in conjunction with lowstretch elastic self-adhesive tapes. It protects, supports and relieves vulnerable, injured or damaged parts of a functional unit. It permits selective loading within the pain-free area of movement, but prevents extreme or painful movements.

However, the application of such dressings requires expert skill and experience and for this reason cannot generally be done by lay persons with no taping experience.

As regards the metacarpophalangeal joint, which is often exposed to very considerable mechanical stress, especially when performing sporting activities, which stress can lead to distortions and contusions, but also to overload irritation of the capsule, the expert nevertheless requires a ready-made bandage which is of a simple construction and at the same time can be applied without problems, and which, especially in the case of minor injuries, has a positive influence on the healing process.

The same also applies to the wrist, so that the demands made of the ready-made bandage are the same as those in the case of the metacarpophalangeal joint.

However, such a ready-made bandage should also be able to be applied by the lay person, affording the after an economic and less time-intensive aid by means of the ready-made bandage.

The object of the invention was therefore to make available a ready-made bandage which, because of its construction, its material and its properties, is suitable for supporting the healing process in injuries of the metacarpophalangeal joint or wrist by restricting the stretching or bending capacity, and which in addition can be easily applied by the user.

SUMMARY OF THE INVENTION

This object is achieved by means of a ready-made bandage having a self-adhesive coating on at least one side, for restricting stretching or bending of the metacarpophalangeal joint and/or of the wrist, comprising an oblong strip (1) having a head area (13), a bottom area (12) and two longitudinal sides, a short rein (41,42) arranged on at least one of the two longitudinal sides, enclosing an angle of between 30° and 150° with the oblong strip, which is applied to the finger in question.

Furthermore, at the bottom area of the oblong strip, a first rein can be arranged on at least one of the two longitudinal sides, which first rein encloses an angle of between 30° and 150° with the oblong strip and is applied in a circle round the lower arm proximal to the wrist.

DETAILED DESCRIPTION

Advantageously, the first rein and/or the short rein is arranged at an angle of 90° to the oblong strip. This also applies in the case where, instead of one first rein, two or more first reins are provided, or where, instead of one short rein, two or more short reins are provided.

Furthermore, the oblong strip can narrow starting from the bottom area towards the head area.

In a first preferred embodiment of the ready-made bandage according to the invention which is used for restricting bending of the metacarpophalangeal joint and of the wrist, and in which a first rein and a short rein are fitted in each case on the oblong strip on each of the two longitudinal sides, the oblong strip is about 12 cm to 30 cm long, and, at the transverse side in the bottom area, is 3 cm to 7 cm wide, and, at the transverse side in the head area, is 1 cm to 3 cm wide, the first reins are each about 5 cm to 30 cm long and 2 cm to 6 cm wide, and the short reins are each about 3 cm to 6 cm long and 1 cm to 3 cm wide.

The dimensions of the ready-made bandage are of course adapted to the size of the hand on which the ready-made bandage is being applied. For the average adult hand, the individual parts of the ready-made bandage have the following sizes:

The oblong strip is about 20 cm long, 6 cm wide on the transverse side in the bottom area, and 2 cm wide on the transverse side at the head area.

The first reins are 22 cm long and 5 cm wide.

The short reins are 5 cm long and 2 cm wide.

All the strips and reins can additionally have rounded corners in order to reduce the risk of unintentional detachment of the adhered ready-made bandage.

At the middle area of the oblong strip, a second rein can be arranged likewise on at least one of the two longitudinal sides, which second rein encloses an angle of between 30° and 150° with the oblong strip and is applied on the palmar surface of the hand.

The first rein, the second rein and/or the short rein are advantageously arranged at an angle of 90° to the oblong strip. This also applies in the case where, instead of a first or second rein, two or more reins are in each case provided, or where, instead of one short rein, two short reins are provided.

Furthermore, the oblong strip can narrow starting from the middle area towards the head area.

In a second preferred embodiment of the ready-made bandage according to the invention which is used for restricting stretching of the metacarpophalangeal joint and of the wrist, and in which a first rein, a second rein and a short rein are in each case fitted on the oblong strip on each of the two longitudinal sides, the oblong strip is about 12 cm to 30 cm long, and, at the transverse side in the bottom area, is 3 cm to 6 cm wide, and, at the transverse side in the head area, is 1 cm to 3 cm wide, the narrowing of the oblong strip starting after approximately 6 cm to 22 cm measured from the transverse side in the bottom area, the first reins are each about 5 cm to 30 cm long and 2 cm to 6 cm wide, the second reins are each about 5 to 30 cm long and 2 cm to 6 cm wide, and the short reins are each about 3 cm to 6 cm long and 1 cm to 3 cm wide.

The dimensions of the ready-made bandage are of course adapted to the size of the hand on which the ready-made bandage is being applied. For the average adult hand, the individual parts of the ready-made bandage have the following sizes:

The oblong strip is about 18 cm long, 6 cm wide on the transverse side in the bottom area, and 2 cm wide on the transverse side at the head area, the narrowing of the oblong strip starting after 12 cm measured from the transverse side in the bottom area.

The first reins are 22 cm long and 5 cm wide.

The second reins are 22 cm long and 3.75 cm wide.

The short reins are 4 cm long and 2 cm wide.

All the strips and reins can additionally have rounded corners in order to reduce the risk of unintentional detachment of the adhered ready-made bandage.

It has proven particularly advantageous for cuttings or recesses to be provided at the points where the oblong strip, the first reins, the second reins and/or the short reins meet. These cuttings prevent the ready-made bandage from tearing at the points which have the highest loading, particularly during application. Alternatively, the recesses increase the flexibility of the ready-made bandage, so that alternatively application is made easier.

Again preferably, the self-adhesive ready-made bandage according to the invention is of a non-elastic woven fabric or knitted fabric. Elastic or plastic components in the longitudinal direction or transverse direction of the support material can sometimes also advantageously influence user comfort. Furthermore, nonwovens or foams or paper can also be used if these have sufficient strength.

The support material can preferably be of cotton and can additionally have a maximum tensile force of not less than 50 N/cm and a maximum tensile force extension of less than 20%.

On the side applied to the skin, the ready-made bandage is coated with one of the known good self-adhesive compositions based on rubber (preferably a zinc rubber composition) or synthetic polymers.

The self-adhesive composition can include solvent, dispersion/emulsion systems, but 100% self-adhesive composition systems can also be used. The compositions advantageously have other properties such as good skin compatibility or permeability to air and water vapour.

To achieve the stated effects, the self-adhesive composition can be applied partially at about 120 g/m$^2$, for example using thermal screen printing with a 14-mesh screen stencil with a screen thickness of 300 μm.

Prior to the bandage being used, the adhesive layer is covered with an anti-adhesive sheet material, for example siliconized paper, which can additionally be perforated for better use, or a foil of plastic.

The material can in this case be divided up into a plurality of sections in order to facilitate application of the ready-made bandage through successive detachment of the individual sections.

The ready-made bandage can be used universally for restricting stretching or bending of the metacarpophalangeal joint or of the wrist.

The blank of the ready-made bandage depends on which hand the ready-made bandage is intended for. Accordingly, there are two mirror-symmetrical configurations of the ready-made bandage according to the invention.

A particularly advantageous embodiment of the ready-made bandage according to the invention, and its use, are explained in greater detail with reference to the figures described hereinbelow.

Provided at the head area (13) of the oblong strip (1) there is a short rein (41) which has a rectangular shape and is arranged at an angle of 90° to the orientation of the oblong strip (1).

To apply the ready-made bandage, in each case the anti-adhesive material is first removed from the section of the ready-made bandage to be applied.

The oblong strip (1) can then be applied flat on the palmar surface of the hand so that it runs from the middle finger concerned here, over the wrist and as far as the lower arm. Here, the wrist should have a flexion of at least 30°. The short rein (31) is wound tightly round the middle finger in a circle, enclosing at least part or preferably all of the finger. Adequate shaping of the ready-made dressing is advantageous.

Figure 1:
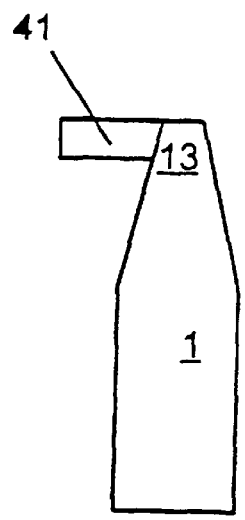
FIG. 1 shows the ready-made bandage in a simplified design thereof. The ready-made bandage (1) is made up of several sections. The central section is formed by an oblong strip (1) which narrows towards the head area (13).
Figure 2:
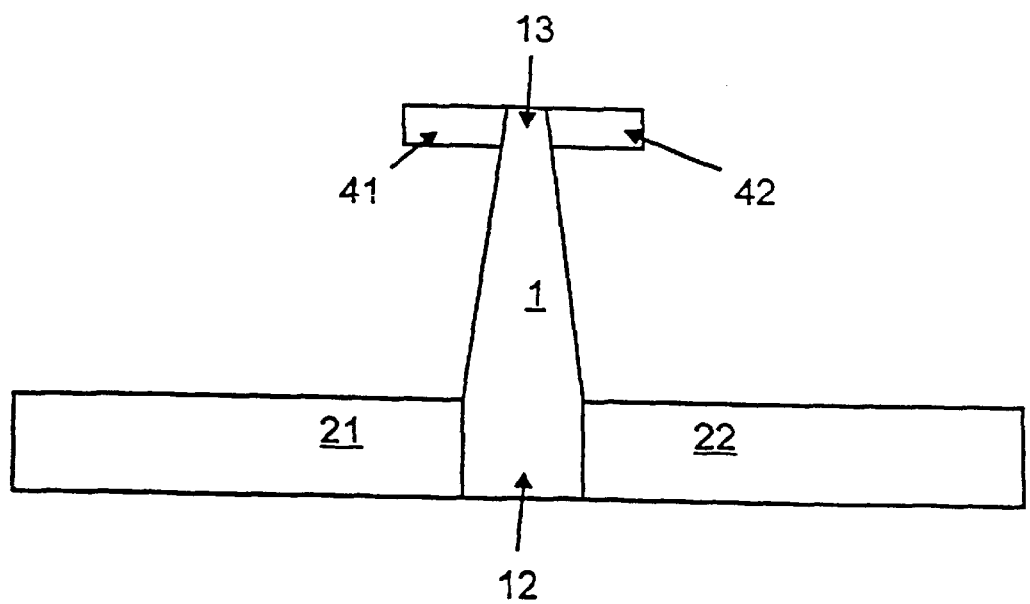

FIG. 2 shows the ready-made bandage in the first preferred embodiment. The central section is formed by an oblong strip (1) which narrows towards the head area (13). At the bottom area (12) of the oblong strip (1), reins (21, 22) are in each case fitted on both longitudinal sides at right angles to the oblong strip (1), which reins have an essentially rectangular shape.

Two short reins (41, 42) are furthermore provided at the head area (13) of the oblong strip (1), which reins likewise have a rectangular shape and are arranged at an angle of 90° to the oblong strip (1), but have a smaller surface area than the reins (21, 22).

To apply the ready-made bandage, in each case the anti-adhesive material is first removed from the section of the ready-made bandage to be applied.

The oblong strip (1) can then be applied on the dorsal surface of the hand so that it runs from the middle finger concerned here, over the wrist and as far as the lower arm. Here, the wrist should have a flexion of at least 30°. The short reins (41, 42) are wound tightly round the middle finger, distally of the metacarpophalangeal joint, enclosing at least part or preferably all of the finger.

The reins (21, 22) are guided in a circle round the lower arm, proximal to the wrist, and secured.

The carefully applied ready-made bandage is able to restrict the bending capacity of the middle finger and of the wrist, and an additionally applied anchor strip round the lower arm can further heighten the effect of the ready-made bandage.

Figure 3:
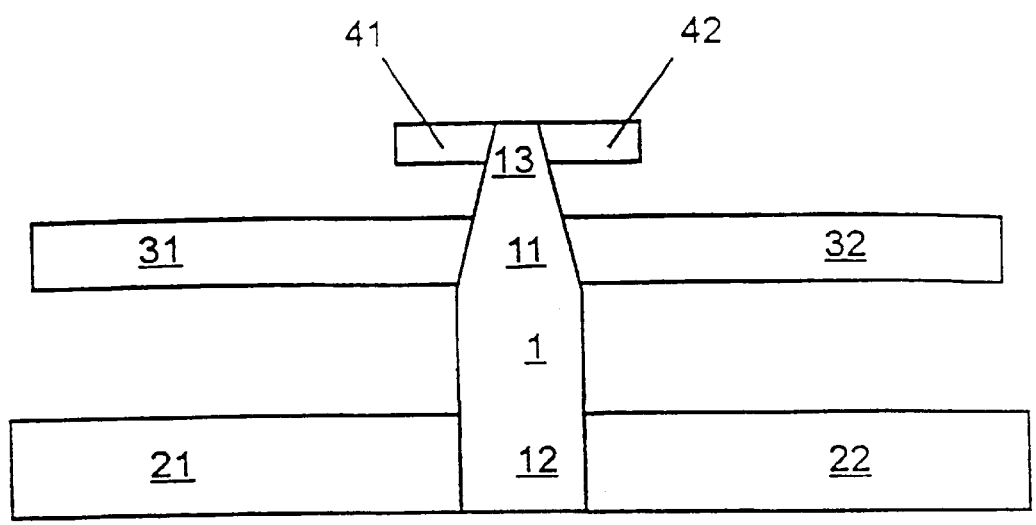

FIG. 3 shows the ready-made bandage in the second preferred embodiment. The central section is formed by an oblong strip (1). At the bottom area (12) of the oblong strip (1), first reins (21, 22) are in each case fitted on both longitudinal sides at right angles to the oblong strip (1), which reins have an essentially rectangular shape. The oblong strip (1) narrows starting from the middle area (11) towards the head area (13). At the middle area (11), second reins (31, 32) are furthermore present on both longitudinal sides and at an angle of 90° to the oblong strip (1). The second reins (31, 32) are also essentially rectangular in shape, but they have smaller dimensions than the first reins (21, 22).

Also provided at the head area (13) of the oblong strip (1) are two short reins (41, 42) which likewise have a rectangular shape and are arranged at an angle of 90° to the oblong strip (1), but which have a smaller surface area than the second reins (31, 32).

To apply the ready-made bandage, in each case the anti-adhesive material is first removed from the section of the ready-made bandage to be applied.

The oblong strip (1) can then be applied on the palmar surface of the hand so that it runs from the middle finger concerned here, over the wrist and as far as the lower arm. Here, the wrist should have a flexion of at least 30°.

The short reins (41, 42) are wound tightly round the middle finger, distally of the metacarpophalangeal joint, enclosing at least part or preferably all of the finger.

The first reins (21, 22) are guided in a circle round the lower arm, proximal to the wrist, and secured.

The second reins (31, 32) are guided from the palmar surface of the hand to the back of the hand and are at all times pressed firmly on the corresponding areas of skin.

The carefully applied ready-made bandage is able to restrict the stretching capacity of the middle finger and of the wrist, and an additionally applied anchor strip round the lower arm can further heighten the effect of the ready-made bandage.

What is claimed is:

1. A ready-made bandage having a self-adhesive coating on at least one side, for restricting stretching or bending of the metacarpophalangeal joint, the wrist, or both, comprising an oblong strip adapted to run from a finger of a human hand, over the wrist and as far as the lower arm, and having a head area, a bottom area and two longitudinal sides, a short rein arranged on at least one of the two longitudinal sides, enclosing an angle of between 30° and 150° with the oblong strip, which is adapted to be applied to said finger.

2. Self-adhesive ready-made bandage according to claim 1, wherein, at the bottom area of the oblong strip, a first rein is arranged on at least one of the two longitudinal sides, encloses an angle of between 30° and 150° with the oblong strip and is adapted to be applied in a circle round the lower arm proximal to the wrist.

3. Self-adhesive ready-made bandage according to claim 2, wherein the first rein, the short rein, or both are arranged at an angle of 90° to the oblong strip.

4. Self-adhesive ready-made bandage according to claim 1, wherein the oblong strip narrows starting from the bottom area towards the head area.

5. Self-adhesive ready-made bandage according to claim 2, wherein the two first reins and two short reins are fitted in each case on both longitudinal sides of the oblong strip.

6. Self-adhesive ready-made bandage according to claim 5, wherein the oblong strip is 12 cm to 30 cm long, and, at the transverse side in the bottom area, is 3 cm to 7 cm wide, and, at the transverse side in the head area, is 1 cm to 3 cm wide, the first reins are about 5 cm to 30 cm long, and are 2 cm to 6 cm wide, the short reins are about 3 cm to 6 cm long, and are 1 cm to 3 cm wide.

7. Self-adhesive ready-made bandage according claim 2, wherein at the middle area of the oblong strip, a second rein is arranged on at least one of the two longitudinal sides, encloses an angle of between 30° and 150° with the oblong strip and is adapted to be applied on the palmar surface of the hand.

8. Self-adhesive ready-made bandage according to claim 7, wherein the first rein, the second rein, the short rein or all of said rains are arranged at an angle of 90° to the oblong strip.

9. Self-adhesive ready-made bandage according to claim 2, wherein the oblong strip narrows starting from the middle area towards the head area.

10. Self-adhesive ready-made bandage according to claim 5, wherein two first reins, two second reins and two short reins are fitted in each case on both longitudinal sides of the oblong strip.

11. Self-adhesive ready-made bandage according to claim 10, wherein the oblong strip is 12 cm to 30 cm long, and, at the transverse side in the bottom area, is 3 cm to 7 cm wide, and, at the transverse side in the head area, is 1 cm to 3 cm wide, the narrowing of the oblong strip starting after approximately 6 cm to 22 cm, measured from the transverse side at the bottom area, the first reins are about 5 cm to 30 cm long, and are 2 cm to 6 cm wide, the second reins are about 5 cm to 30 cm long, and are 2 to 6 cm wide, the short reins are about 3 cm to 6 cm long, and are 1 cm to 3 cm wide.

12. Self-adhesive ready-made bandage according to claim 11, wherein cuttings are provided at the points where the oblong strip, the first reins, the second reins and/or the short reins meet.

13. Self-adhesive ready-made bandage according to claim 1, wherein the ready-made bandage is of a non-elastic support material.

14. Self-adhesive ready-made bandage according to claim 13, wherein the non-elastic support material is a woven cotton fabric and has a maximum tensile force of not less than 50 N/cm and a maximum tensile force extension of less than 20%.

15. Self-adhesive ready-made bandage according to claim 1, wherein the ready-made bandage is covered, on its self-adhesive side, with anti-adhesive material.

16. Method for restricting stretching or bending of the metacarpophalangeal joint or of the wrist, which comprises applying to said metacarpophalangeal joint or wrist the self-adhesive ready-made bandage according to claim 1.

* * * * *